US00PP11836P2

(12) United States Plant Patent
Radler

(10) Patent No.: US PP11,836 P2
(45) Date of Patent: Apr. 10, 2001

(54) SHRUB ROSE PLANT NAMED 'RADRAZZ'

(75) Inventor: William J. Radler, Greenfield, WI (US)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/229,323

(22) Filed: Jan. 13, 1999

(51) Int. Cl.[7] ..... A01H 5/00
(52) U.S. Cl. ..... Plt./108
(58) Field of Search ..... Plt./102, 107, 108, Plt./149, 150, 151

(56) References Cited

U.S. PATENT DOCUMENTS

P.P. 3,995 * 12/1976 Warriner ..... Plt./141
P.P. 4,224 * 3/1978 Paolino ..... Plt./130
P.P. 4,225 * 3/1978 Buck ..... Plt./137

OTHER PUBLICATIONS

UPOV–ROM, Feb. 1999, Plant Variety Database, GTI Jouve Retrieval Software, citation for 'Razzle Dazzle', pp 3995.*
American Association of Nurseryman, 1990, "Plant Patent Directory" p. 123, numerical listing of plant patents.*
Haring, ed., 1986, "Modern Roses 9", The American Rose Society, Shreveport, LA., p. 44.*

* cited by examiner

*Primary Examiner*—Howard J. Locker
(74) *Attorney, Agent, or Firm*—Burns, Doane, Swecker & Mathis, L.L.P.

(57) ABSTRACT

A new and distinct variety of landscape shrub rose plant is provided which forms in abundance on a substantially continuous basis attractive single blossoms that are red in coloration. The vegetation is vigorous and the growth habit is round and bushy. Attractive ornamental satiny green foliage is formed. Excellent disease resistance to blackspot is exhibited. Additionally, the new variety is particularly well suited for growing as distinctive ornamentation in the landscape.

1 Drawing Sheet

SUMMARY OF THE INVENTION

The new variety of *Rose hybrida* landscape shrub rose plant of the present invention was created by artificial pollination wherein two parents were crossed which previously had been studied in the hope that they would contribute the desired characteristics. The female parent (i.e., the seed parent) was a seedling of the 'Carefree Beauty' variety (U.S. Plant Pat. No. 4,225). The male parent (i.e., the pollen parent) of the new variety was a seedling of the 'Razzle Dazzle' variety (U.S. Plant Pat. No. 3,995). The parentage of the new variety can be summarized as follows:

'Carefree Beauty' Seedling×'Razzle Dazzle' seedling.

The seeds resulting from the above pollination were sown and small plants were obtained which were physically and biologically different from each other. Selective study resulted in the indentification of a single plant of the new variety.

It was found that the new variety of landscape shrub rose plant of the present invention possesses the following combination of characteristics:

(a) Abundantly and substantially continuously forms attractive single blossoms that are red in coloration,
(b) Exhibits a round and bushy growth habit,
(c) Forms vigorous vegetation,
(d) Forms attractive ornamental green foliage with a satiny finish, and
(e) Exhibits excellent resistance to blackspot.

A new rose variety is provided having attractive red blooms, combined with substantially continuous blooming and blackspot resistance. The blooming cycle is believed to be one of the longest observed to date for a rose plant.

The new variety well meets the needs of the horticultural industry. It can be grown to advantage as attractive ornamentation in parks, gardens, public areas, and residential landscapes. Accordingly, it is particularly well suited for growing in the landscape. The red blossoms contrast nicely with the satiny green foliage.

The characteristics of the new variety have been found at Wasco, Calif. to be homogeneous and stable and are strictly transmissible by asexual propagation such as budding, grafting, and cuttage from one generation to another.

The new variety has been named the 'Radrazz' variety.

BRIEF DESCRIPTION OF THE PHOTOGRAPH

The accompanying photographs shows, as nearly true as it is reasonably possible to make the same in a color illustration of this character, typical specimens of the plant and plant parts of the new variety. The rose plants of the new variety illustrated herein were two years of age and were grown outdoors during July on their own roots at West Grove, Pa. Dimensions in millimeters are indicated at the right of the photograph.

FIG. 1—illustrates a specimen of a young shoot;

FIG. 2—illustrates a specimen of a floral bud with foliage before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the initial course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates specimens of main branches with foliage at the top;

FIG. 14—illustrates a specimen of a leaf with three leaflets—plan view—upper surface;

FIG. 15—which is located at the lower right portion of the photograph illustrates a specimen of a leaf with five leaflets—plan view—upper surface;

FIG. 16—illustrates a specimen of a leaf with seven leaflets—plan view—upper surface; and FIG. 17—illustrates specimens of mature floral petals.

DETAILED DESCRIPTION

The chart used in the identification of colors is that of The Royal Horticultural Society (R.H.S. Colour Chart). The description is based on two year-old specimens of the new variety during October while grown outdoors on their own roots at West Grove, Pa.

Class: Landscape shrub rose.

Plant:

*Height*.—Approximately one meter on average at the end of the growing season.

*Width*.—Approximately one meter on average at the end of the growing season.

*Habit*.—Round, and bushy.

Branches:

*Color*.—Young stems: Near Yellow-Green Group 144B with some highlights of Red Group 53A. Adult wood: Yellow-Green Group 144B suffused with Greyed-Purple Group 184A.

*Thorns*.—Size: Approximately 1 to 1.5 cm. In length on average with some smaller bristles/prickles near the peduncle. Quantity: As illustrated. Color: Greyed-Purple Group 184B.

Leaves:

*Stipules*.—Parallel with auricle facing outward.

*Petioles*.—Under surface: Yellow-Green Group 144B with highlights of Greyed-Purple Group 184A and some prickles. Upper surface: Yellow-Green Group 144B.

*Leaflets*.—Number: 3, 5, and 7. Shape: Ovate with a serrulate margin, rounded base, and acuminate tip. Serration: As illustrated. Texture: Smooth. Size: Approximately 7 cm in length. Overall appearance: Very dense, leathery, and medium green in coloration, with a satiny finish. Color (young foliage): Upper surface: Greyed-Purple Group 187A with highlights of Green Group 141D. Under surface: Greyed-Purple Group 187B. Color (adult foliage): Upper surface: Commonly between Yellow-Green Group 147A and Green Group 136A. Under surface: Yellow-Green Group 147B with some Yellow-Green Group 148D.

Inflorescence:

*Number of flowers*.—Commonly approximately 4 blooms on average in a cluster.

*Peduncle*.—Medium green, Green Group 141D, with some prickles, and approximately 4 cm. in length on average.

*Sepals*.—Upper surface: between Yellow-Green Group 144A and Yellow-Green Group 144B. Upper surface: Yellow-Green Group 144B with areas of White Group 155D and some pubescence.

*Buds*.—Shape: Slender (as illustrated). Length: Approximately 2.5 cm. on average. Size: Small to medium. Color (when opening): Upper surface: Commonly between Red Group 52A and Red Group 55C. Under surface: Commonly between Red Group 53C and Red Group 53D.

*Flower*.—Form: Single and informal. Diameter: Approximately 7 cm. on average. Color (when opening begins): Upper surface: Crimson, near Red Group 52A. Under surface: Between Red Group 52B and Red Group 53D. Color (when blooming): Upper surface: Between Red Group 53C and Red Group 53D. Under surface: Red Group 55A with highlights of Red Group 55B and lighter at the center. Color (at end of blooming): Upper surface: Between Red Group 53D and Red Group 54A and lighter at the center. Under surface: Red Group 55A with highlights of Red Group 55B and lighter at the center. Fragrance: Mild spice. Petal form: Wedge-shaped with a curled apex. Petal number: Approximately 10 on average. Lasting quality: Blossoms commonly last approximately two weeks on the plant and approximately three weeks when cut and placed in a vase. Petal drop: Very good, the petals drop cleanly and freely. Stamen number: Approximately 65 on average. Anthers: Greyed-Yellow Group 162B in coloration. Filaments: Red Group 48D in coloration. Pistils: are separate and free, and number Approximately 27 on average. Stigmas: Yellow Group 13C in coloration. Styles: Red Group 45B in coloration. Receptacle: Achenes stand on the bottom and wall.

Development:

*Vegetation*.—Vigorous and strong.

*blossoming*.—Abundant and substantially continuous.

*Resistance to diseases*.—Excellent with respect to blackspot and rust.

*Formation of hips/seeds*.—Sparse.

I claim:

1. A new and distinct variety of landscape shrub rose plant characterized by the following combination of characteristics:

(a) abundantly and substantially continuously forms attractive single blossoms that are red in coloration,
(b) exhibits a round and bushy growth habit;
(c) forms vigorous vegetation,
(d) forms attractive ornamental green foliage with a satiny finish, and
(e) exhibits excellent resistance to blackspot;

substantially as herein shown and described.

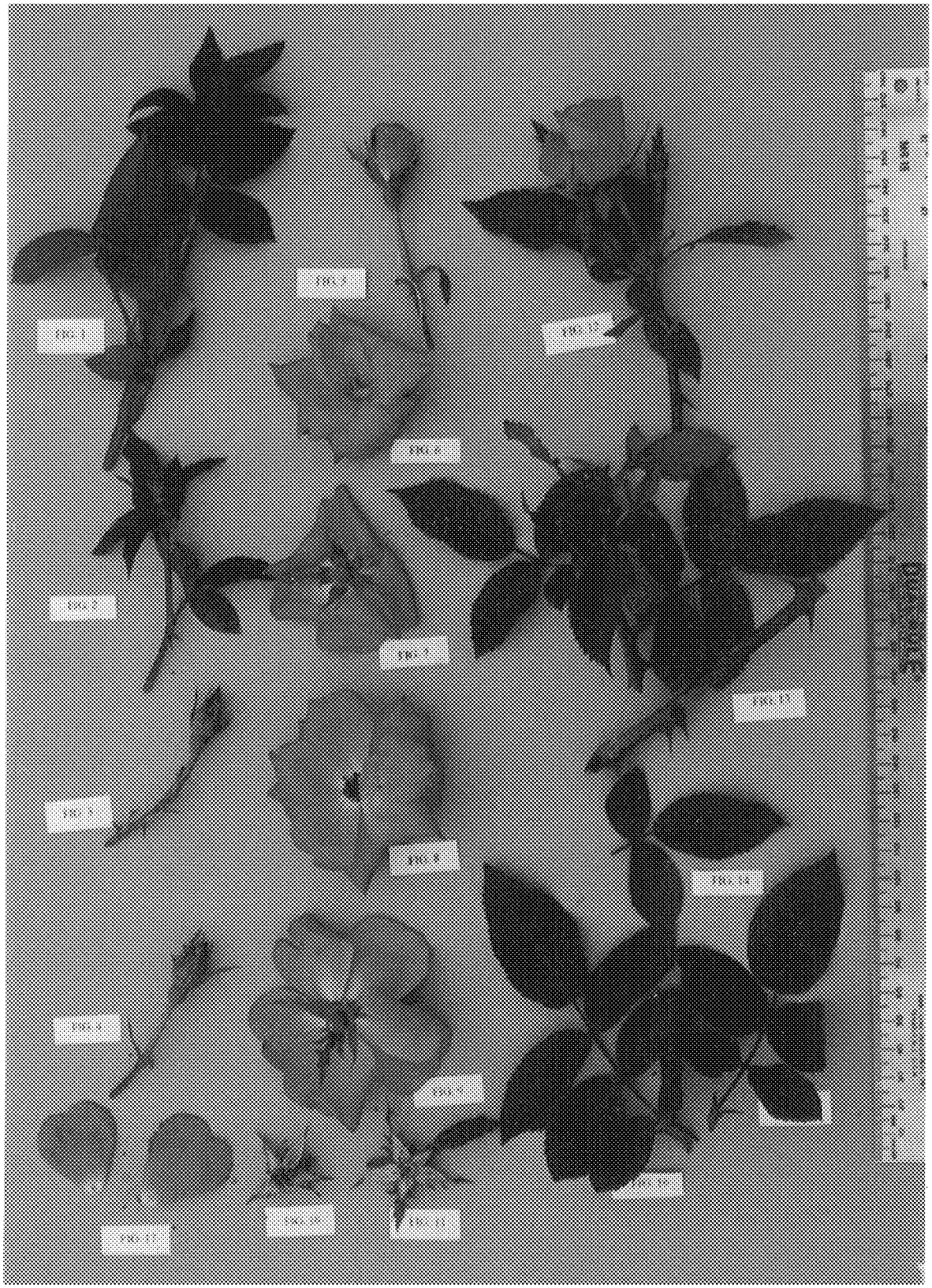

* * * * *